United States Patent
Baran, Jr. et al.

(10) Patent No.: US 8,323,360 B2
(45) Date of Patent: Dec. 4, 2012

(54) METHOD OF CRYSTALLIZATION

(75) Inventors: Jimmie R. Baran, Jr., Prescott, WI (US); William J. Hunt, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 218 days.

(21) Appl. No.: 12/993,746

(22) PCT Filed: Jun. 26, 2009

(86) PCT No.: PCT/US2009/048739
§ 371 (c)(1),
(2), (4) Date: Nov. 19, 2010

(87) PCT Pub. No.: WO2010/002712
PCT Pub. Date: Jan. 7, 2010

(65) Prior Publication Data
US 2011/0077392 A1    Mar. 31, 2011

Related U.S. Application Data

(60) Provisional application No. 61/076,866, filed on Jun. 30, 2008.

(51) Int. Cl.
*B01D 9/00* (2006.01)
*C30B 17/00* (2006.01)
(52) U.S. Cl. .................................. 23/301; 23/300
(58) Field of Classification Search .................. None
See application file for complete search history.

(56) References Cited

U.S. PATENT DOCUMENTS

| | | | |
|---|---|---|---|
| 2,801,185 A | 7/1957 | Iler |
| 4,455,205 A | 6/1984 | Olson |
| 4,478,876 A | 10/1984 | Chung |
| 4,486,504 A | 12/1984 | Chung |
| 4,491,508 A | 1/1985 | Olson |
| 4,522,958 A | 6/1985 | Das |
| 5,037,579 A | 8/1991 | Matchett |
| 5,258,225 A | 11/1993 | Katsamberis |
| 6,329,058 B1 | 12/2001 | Arney |
| 6,432,526 B1 | 8/2002 | Arney |
| 6,586,483 B2 | 7/2003 | Kolb |
| 6,833,192 B1 | 12/2004 | Caruso |
| 6,875,449 B1 | 4/2005 | Marriott |
| 7,211,239 B2 | 5/2007 | Muller |
| 7,220,434 B2 | 5/2007 | Desai |
| 7,304,062 B2 | 12/2007 | Dominianni |
| 7,314,528 B2 | 1/2008 | Koivikko |
| 7,329,319 B2 | 2/2008 | Myerson |
| 7,329,592 B2 | 2/2008 | Myerson |
| 2003/0152500 A1 | 8/2003 | Dalziel |
| 2004/0219221 A1 | 11/2004 | Moore |

FOREIGN PATENT DOCUMENTS

| | | |
|---|---|---|
| DE | 198 44 227 A1 | 4/2000 |
| WO | WO03/002225 | 1/2003 |
| WO | WO2005/062720 | 7/2005 |
| WO | WO2005/066075 | 7/2005 |
| WO | WO2006/131497 | 12/2006 |
| WO | WO2007/020064 | 2/2007 |
| WO | WO2008/021142 | 2/2008 |

OTHER PUBLICATIONS

Linsenbuhler, M. et. al., *Powder Technology*, 158, 2003, p. 3-20.
*Crystallization Technology Handbook*, ed. A. Mersmann, Marcel Decker, Inc., New York, 1995.
*Industrial Crystallization from Solutions*, Nyvlt, J., CRC Press, Butterworth & Company, 1971.

*Primary Examiner* — Layla Bland
(74) *Attorney, Agent, or Firm* — Stephen L. Crooks

(57) ABSTRACT

A method of crystallization is provided. The method includes providing a solution comprising a solute dissolved in a first solvent. The method includes providing a dispersion comprising a plurality of nanoparticles in a second solvent. The first solvent and the second solvent are mutually miscible. The method includes combining the solution and the dispersion to form a mixture. The nanoparticles remain dispersed in the mixture and the solute remains dissolved in the mixture at or below a saturation concentration. The method includes cooling the mixture such that the solute exceeds the saturation concentration forming crystals in the presence of the dispersed nanoparticles. The method includes separating the crystals from the mixture, wherein the nanoparticles remain dispersed in the mixture.

19 Claims, 3 Drawing Sheets

US 8,323,360 B2

METHOD OF CRYSTALLIZATION

CROSS REFERENCE TO RELATED APPLICATIONS

This application is a national stage filing under 35 U.S.C. 371 of PCT/US2009/048739, filed Jun. 26, 2009, which claims priority to Provisional Application No. 61/076,866, filed Jun. 30, 2008, the disclosure of which is incorporated by reference in its/their entirety herein.

FIELD

The present disclosure relates to methods for crystallizing solutes.

BACKGROUND

Crystallization is the conversion of a substance or several substances from an amorphous solid, liquid, or gaseous state to the crystalline state. Generally, parameters such as crystal size distribution, median crystal size, crystal purity, and crystal shape are considered for crystals.

Crystallization of a molecule from a liquid can depend on the degree of saturation in the liquid as generated by cooling, evaporation, drowning out, or by a reaction. A liquid or a melt can be used for crystallizing materials.

A solution having a crystallized material capable of crystallization generally achieves a saturated concentration or supersaturated concentration for crystals to form or for existing crystals to grow. Crystals can grow from surfaces of containers or from seed crystals having irregular shapes or sizes. Crystals having undesirable variations in crystal size, and crystal size distribution are problematic, for example, in pharmaceutical formulations employing such crystals. There is a need for methods for forming crystals having controlled crystal sizes and crystal size distributions.

SUMMARY

The present disclosure describes methods of crystallization. More specifically, methods are provided for forming crystals from mixtures having dispersed nanoparticles.

In a first aspect, a method of crystallization is provided. The method includes providing a solution comprising a solute dissolved in a first solvent. The method includes providing a dispersion comprising a plurality of nanoparticles in a second solvent. The first solvent and the second solvent are mutually miscible. The method includes combining the solution and the dispersion to form a mixture. The nanoparticles remain dispersed in the mixture and the solute remains dissolved in the mixture at or below a saturation concentration. The method includes cooling the mixture such that the solute exceeds the saturation concentration forming crystals in the presence of the dispersed nanoparticles. The method includes separating the crystals from the mixture such that the nanoparticles remain dispersed in the mixture.

In a second aspect, a method of crystallization is provided. The method includes providing a solution comprising a solute dissolved in a first solvent. The method includes providing a dispersion comprising a plurality of nanoparticles in a second solvent. The first solvent and the second solvent are mutually miscible. The method includes combining the solution and the dispersion to form a mixture. The nanoparticles remain dispersed in the mixture and the solute remains dissolved in the mixture at or below a saturation concentration. The method includes evaporating the first solvent or the second solvent or combinations thereof from the mixture such that the solute exceeds the saturation concentration forming crystals in the presence of the dispersed nanoparticles. The method includes separating the crystals from the mixture such that the nanoparticles remain dispersed in the mixture.

DETAILED DESCRIPTION

Figure 1:
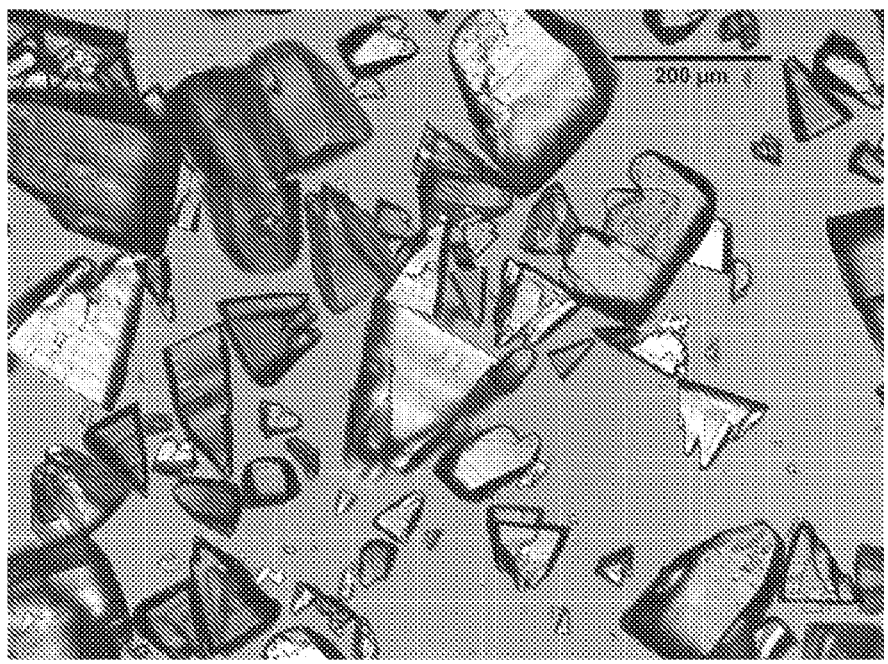
FIG. 1 is an optical micrograph of lactose crystals formed in the absence of nanoparticles.

For the following defined terms, these definitions shall be applied, unless a different definition is given in the claims or elsewhere in the specification.

The term "nanoparticle" will generally refer to particles, groups of particles, particulate molecules (i.e., small individual groups of loosely associated groups of molecules) and groups of particulate molecules that while potentially varied in specific geometric shape have and effective, or average, diameter that is less than 1 micrometer.

The term "surface modified nanoparticle" refers to a nanoparticle that includes surface groups attached to the surface of the nanoparticle.

The term "mutually miscible" refers to capable of mixing in any ratio without a separation of phases.

The recitation of numerical ranges by endpoints includes all numbers subsumed within that range (e.g., 1 to 5 includes 1, 1.5, 2, 2.75, 3, 3.8, 4, and 5).

As included in this specification and the appended claims, the singular forms "a", "an", and "the" include plural referents unless the content clearly dictates otherwise. Thus, for example, reference to a composition containing "a compound" includes a mixture of two or more compounds. As used in this specification and appended claims, the term "or" is generally employed in its sense including "and/or" unless the content clearly dictates otherwise.

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present disclosure. At the very least, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains errors necessarily resulting from the standard deviations found in their respective testing measurements.

Solutes can be crystallized from a mixture comprising a solution and dispersed nanoparticles. The solute can be crystallized from the mixture at processing conditions where the solute exceeds the saturation concentration and forms crystals having controlled morphologies. Crystals formed from the mixtures can be altered, for example, based on the presence of nanoparticles, the surface modification on the nanoparticles, the size of the nanoparticles, and the weight percent of the nanoparticles relative to the solute in the mixture. Other factors known in the art can also influence the formation of solute crystals in the presence of nanoparticles.

In the method of the present disclosure, solutes typically having at least one crystalline phase are used. The solutes selected to crystallize from a mixture comprising nanoparticles for forming crystals have controlled crystal sizes, controlled crystal size distributions, and the like, or combinations thereof. The term "controlled" refers to crystals formed by the method of the present disclosure having similar crystal sizes and/or crystal size distributions as compared to crystals formed without nanoparticles. Crystals formed by the method of the present disclosure have more uniform shapes (e.g., trigonal, cubic, and others), and are relatively free of extraneous materials (e.g., nanoparticles), satellite crystals (e.g., crystals forming adjacent to other crystals), and twinning crystals (e.g., crystals forming on the top of a crystal).

Crystallizable solutes are generally dissolved (e.g., soluble) in the first solvent for forming a solution up to a saturation concentration. The solubility of the solute in the first solvent is a characteristic physical property referring to the ability for a given solute to dissolve in a first solvent. The solubility of the solute can be measured in terms of the maximum amount of solute dissolved in the first solvent at equilibrium for forming a saturated solution. In some embodiments, the addition of solute to the saturated solution can be achieved under conditions (e.g., temperature) which can affect the solubility of the solute in the first solvent. The concentration of the solute being greater than the saturation concentration can be referred to as a supersaturated solution. At the supersaturated concentration, the dissolved solute can be unstable, thus evoking the condition where the solute can crystallize from the solution.

The solubility of the solute in the first solvent can be determined by the balance of intermolecular forces between the solute and the first solvent, and the entropy change that accompanies the solvation. In some instances, for example, temperature and pressure are factors that can alter the balance of intermolecular forces, thus changing the solubility.

Processing conditions can affect the solubility of the solute in the first solvent for forming a solution. Some processing conditions affecting the solute concentration in the solution include, but are not limited to, cooling, removing a portion of the first solvent, introducing a second solvent where the resulting mixture can exist in a supersaturated state, or combinations thereof. Solute concentrations below a saturation concentration can result in transparent or nearly transparent solutions. With increasing solute concentration, a saturation concentration can be achieved. At the saturation concentration, under the same or similar processing conditions, practically no additional solute can be dissolved in the first solvent.

A change in the processing conditions (e.g., increase in temperature) can alter the solubility and the concentration of the solute in the first solvent. The addition of solute above the saturation concentration can result in a metastable or a supersaturated solution. Similarly, a supersaturated solution can be achieved by the addition of a nonsolvent to a saturated solution thus increasing the concentration of the solute in the first solvent. Other processing conditions can affect the solubility of the solute in the first solvent.

Suitable solutes for forming crystals according to the method of the present disclosure include, for example, mono- and di-saccharides, polysaccharides, alcohols, esters, active pharmaceutical ingredients, adjuvants, pigments, colorants, fillers, inorganic salts, organic salts, and the like, or combinations thereof. Some suitable mono- and di-saccharides include, for example, lactose, α-lactose monohydrate, β-anhydrous lactose, α-anhydrous lactose, maltose, sucrose, mannitol, arabinose, xylitol, dextrose, and the like, or combinations thereof. Suitable polysaccharides include, for example, starches, dextrins, dextrans, and the like, or combinations thereof. Suitable alcohols include, for example, triphenylmethanol, inositol, hexahydroxybenzene, and the like, or combinations thereof.

In one embodiment, the solute is a sugar comprising lactose (i.e., milk sugar). The systematic name for lactose is β-D-galactopyranosyl-(1↔4)β-D-glucopyranose. Lactose can encompass physical, crystalline, amorphous and polymorphic forms of lactose, including, but not limited to, the stereoisomers, α-lactose monohydrate, β-anhydrous lactose, and α-anhydrous lactose, and the like, or combinations thereof. Lactose can be dissolved in protic solvents. The solubility of lactose in some protic solvents can range from highly soluble, partially soluble, or insoluble. The solubility of lactose in some protic solvents is highly soluble. Some examples of protic solvents include, for example, water, methanol, ethanol, isopropanol, and the like, or combinations thereof. In one embodiment, lactose is soluble in water (e.g., first solvent). Lactose is generally insoluble in heptane, hexane, and the like, or combinations thereof. Similarly, lactose can be dissolved in a combination of one or more miscible solvents.

In one embodiment, the solute is triphenylmethanol (i.e. triphenylcarbinol). Triphenyl methanol is an aromatic organic compound that is a white crystalline solid. Triphenylmethanol can be dissolved in some organic solvents. The solubility of triphenylmethanol in some organic solvents is highly soluble. Some examples of useful organic solvents include, for example, toluene, ethanol, benzene, and the like, or combinations thereof. In one embodiment, triphenylmethanol is highly soluble in toluene (e.g., first solvent). Similarly, triphenylmethanol can be dissolved in a combination of two or more miscible solvents.

In the method of the present disclosure, the first solvent is used to dissolve a solute to form a solution. The first solvent is selected for which the solute is highly soluble. The selected first solvent can dissolve the solute at or below a saturation concentration. The solubility of the solute in the first solvent can be altered under certain processing conditions sufficient for the solution to comprise a higher concentration of solute. The first solvent selected for dissolving the solute can have a measure saturation concentration in the first solvent. The solubility of the solute can be altered, for example, by temperature, presence of nonsolvents, evaporation of a solvent, and the like.

Some examples of solvents useful for dissolving solutes include, for example, aqueous and nonaqueous solvents. Suitable examples of aqueous and nonaqueous solvents include, for example, water, alcohols, aliphatic hydrocarbons, aromatic hydrocarbons, ketones, esters, fluorocarbons, ethers, hydrofluorocarbons, supercritical fluids, and the like or combinations thereof.

In some embodiments, the first solvent can be a combination of two or more solvents. The selection of two or more solvents can be based on the miscibility of the two or more solvents and the solubility of the solute in the solvents. The solute can be highly soluble in the two or more solvents. Similarly, the solvents when combined or mixed can form a single phase.

In one embodiment, the first solvent is an aqueous solvent such as water and the solute is lactose. In another embodiment, the first solvent is a nonaqueous solvent (e.g., aromatic hydrocarbon) such as toluene and the solute is triphenylmethanol.

In the method of the present disclosure, a dispersion comprising a plurality of nanoparticles is provided. The nanoparticles are dispersed in a second solvent. The second solvent is selected to i) disperse the nanoparticles, and to ii) be mutually miscible with the first solvent of the mixture. Upon mixing of the solution and the dispersion for forming a mixture, the nanoparticles remain dispersed and are substantially free of agglomeration. In some embodiments, the nanoparticles are surface modified nanoparticles. The surface modified nanoparticles are not soluble in the second solvent or the first solvent. As described above, the second solvent disperses the surface modified nanoparticles and is mutually miscible with the first solvent of the mixture.

In one embodiment, the second solvent and the first solvent of the solution are the same solvent. In another embodiment, the first solvent is not the same as the second solvent; however, the first solvent forms a single phase with the second solvent. The first solvent and the second solvent can be selected such that the solute remains dissolved in the mixture, and the nanoparticles (e.g., modified or unmodified) can remain dispersed when combined for forming a mixture.

The solubility limit of the solute in the second solvent can be considered when forming the mixture. In the mixture, the solute can be soluble in the second solvent, and remain soluble as the concentration of the solute in the mixture changes. The second solvent can be selected such that the solute does not precipitate from the mixture.

Suitable second solvents in the mixture can include, for example, ethanol as a second solvent in combination with water as the first solvent. The solute can be highly soluble in the second solvent in the mixture. The solubility of the solute can change based on the selection of the second solvent. Other suitable combinations of second solvents with first solvents can be made based on the discussion of miscibility and solute solubility above.

In the method of the present disclosure, a dispersion comprising a plurality of nanoparticles and a second solvent is provided. The second solvent is described above. The dispersion is combined with the solution comprising a solute and the first solvent to form a mixture. The crystals of the solute can be formed in the presence of the nanoparticles of the mixture. The nanoparticles can remain dispersed in the mixture as the crystals are separated from the mixture.

Nanoparticles can provide for greater surface area and a greater number of nanoparticles on a weight percent basis as compared to particles having greater dimensions. The availability of more nanoparticles and their small dimensions can provide for an increase of nucleation sites and growth locations for the formation of crystals in some cases. Similarly, nanoparticles can provide for decreased diffusion rates of solute molecules which can result in slower transport of the solute molecules to growing crystal surfaces when the solute exceeds the saturation concentration. In another instance, nanoparticles can provide for reduced diffusion rates which can kinetically constrain the number of solute molecules that can get to a growing crystal and consequently limit the size of the crystal.

A plurality of nanoparticles (inorganic or organic) dispersed in a second solvent can form a dispersion. The nanoparticles can be described without surface modification, with surface modification (i.e., surface modified nanoparticles), and the like, or mixtures and combinations thereof. In one embodiment, surface modified nanoparticles are dispersed in a second solvent. The surface modified nanoparticles are physically or chemically modified and are generally different from the composition of the bulk of the nanoparticles. The surface groups of the nanoparticles preferably are present in an amount sufficient to form a monolayer, preferably a continuous monolayer, on the surface of the particle. The surface groups are present on the surface of the nanoparticles in an amount sufficient to provide nanoparticles that are capable of being dispersed in the second solvent with minimal aggregation or agglomeration.

Suitable inorganic nanoparticles include calcium phosphate, calcium hydroxyapatite, and metal oxide nanoparticles such as zirconia, titania, silica, ceria, alumina, iron oxide, vanadia, zinc oxide, antimony oxide, tin oxide, nickel oxide, and combinations thereof. Suitable inorganic composite nanoparticles include alumina/silica, iron oxide/titania, titania/zinc oxide, zirconia/silica, and combinations thereof. Metals such as gold, silver, or other precious metals can also be utilized as solid particles or as coatings on organic or inorganic nanoparticles. In one embodiment, the nanoparticles comprise silica.

Surface modified nanoparticles or precursors to them may be in the form of a colloidal dispersion. Some of these dispersions are commercially available as unmodified silica starting materials, for example, nano-sized colloidal silicas available under the product designations "NALCO 1040," "NALCO 1050," "NALCO 1060," "NALCO 2326," "NALCO 2327," and "NALCO 2329" colloidal silica from Nalco Chemical Company of Naperville, Ill. Metal oxide colloidal dispersions include colloidal zirconium oxide, suitable examples of which are described, for example, in U.S. Pat. No. 5,037,579 (Matchett), and colloidal titanium oxide, examples of which are described, for example, in U.S. Pat. Nos. 6,329,058 and 6,432,526 (Arney et al.). Such nanoparticles are suitable substrates for surface modification as described below.

Suitable organic nanoparticles include those including organic polymeric nanoparticles, trehalose, amino acids, and the like. A useful class of organic polymeric nanoparticles includes nanospheres that comprise polystyrene, such as those available from Bangs Laboratories, Incorporated of Fishers, Ind. as powders or dispersions. Such organic polymeric nanospheres will generally have median particle sizes ranging from 20 nanometers to not more than 60 nanometers. Another class of organic nanoparticles includes buckminsterfullerenes (fullerenes), dendrimers, branched and hyperbranched "star" polymers such as 4, 6, or 8 armed polyethylene oxide available from Aldrich Chemical Company of Milwaukee, Wis., or Shearwater Corporation of Huntsville, Ala., whose surface has been chemically modified. Specific examples of fullerenes include $C_{60}$, $C_{70}$, $C_{82}$, and $C_{84}$. Specific examples of dendrimers include polyamidoamine (PAMAM) dendrimers of Generations 2 through 10 (G2-G10), also available from Aldrich Chemical Company of Milwaukee, Wis.

It will be understood that the selected surface modified nanoparticles may be used alone or in combination with one or more other nanoparticles (e.g., modified or unmodified) including mixtures and combinations of organic and inorganic nanoparticles. Such combinations may be uniform or have distinct phases, which can be dispersed or regionally specific, such as layered or of a core-shell type structure. The selected nanoparticles, whether inorganic or organic, and in whatever form employed, will generally have a median particle diameter of less than 100 nanometers. In some embodiments, nanoparticles may be utilized having a smaller median effective particle diameter of, for example less than or equal to 50, 40, 30, 20, 15, 10 or 5 nanometers; in some embodiments from 2 nanometers to 20 nanometers; in still other embodiments from 3 nanometers to 10 nanometers. If the chosen nanoparticle or combinations of nanoparticles are themselves aggregated, the maximum preferred cross-sectional dimension of the aggregated nanoparticles will be within any of these stated ranges.

In many cases it may be desirable for the nanoparticles utilized to be substantially spherical in shape. In other applications, however, more elongated shapes by be desired. Aspect ratios less than or equal to 10 are considered preferred, with aspect ratios less than or equal to 3 generally more preferred.

Surface modified or unmodified nanoparticles may be selected such that the nanoparticles are essentially free from a degree of particle association, agglomeration, or aggregation that may interfere with the formation of solute crystals from the mixture. As used herein, particle "association" is defined as a reversible chemical combination due to any of the weaker classes of chemical bonding forces. Examples of particle association include hydrogen bonding, electrostatic attraction, London forces, van der Waals forces, and hydrophobic interactions. As used herein, the term "agglomeration" is defined as a combination of molecules or colloidal particles into clusters. Agglomeration may occur due to the neutralization of the electric charges, and is typically reversible. As used herein, the term "aggregation" is defined as the tendency of large molecules or colloidal particles to combine in clusters or clumps and precipitate or separate from the dissolved state. Aggregated nanoparticles are firmly associated with one another, and require high shear to be broken. Agglomerated and associated particles can generally be easily separated.

The surface of the selected nanoparticles can be chemically or physically modified in some manner. Such modifications to the nanoparticle surface may include, for example, covalent chemical bonding, hydrogen bonding, electrostatic attraction, London forces and hydrophilic or hydrophobic interactions so long as the interaction is maintained at least during the time period required for the nanoparticles to achieve their intended utility. The surface of the nanoparticle may be modified with one or more surface modifying groups. The surface modifying groups may be derived from a myriad of surface modifying agents. Schematically, surface modifying agents may be represented by the following general formula:

A-B     (I)

The A group in Formula I is a group or moiety that is capable of attaching to the surface of the nanoparticle. In those situations where the nanoparticle is processed in solvents, the B group is a compatibilizing group with whatever the first and second solvents used to process the nanoparticles. In those situations where the nanoparticles are not processed in solvent, the B group is a group or moiety that is capable of preventing irreversible agglomeration of the nanoparticles. It is possible for the A and B components to be the same, where the attaching group may also be capable of providing the desired surface compatibility. The compatibilizing group may be reactive, but is generally non-reactive, with the microparticles. It is understood that the attaching composition may be comprised of more than one component or created in more than one step, e.g., the A composition may be comprised of an A' moiety which is reacted with the surface of a nanoparticle, followed by an A" moiety which can then be reacted with B. The sequence of addition is not important, i.e., the A'A"B component reactions can be wholly or partly performed prior to attachment to the nanoparticle. Further description of nanoparticles in coatings can be found in Linsenbuhler, M. et. al., *Powder Technology*, 158, 2003, p. 3-20.

Many suitable classes of surface-modifying agents for modifying the nanoparticle surface are known, and include silanes, organic acids, organic bases, and alcohols, and combinations thereof.

In one embodiment, surface-modifying agents include silanes. Examples of silanes include, for example, organosilanes such as alkylchlorosilanes; alkoxysilanes (e.g., methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, isooctyltrimethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy)silane, vinyltris(isopropenoxy)silane, and vinyltris(2-methoxyethoxy)silane; trialkoxyarylsilanes; isooctyltrimethoxy-silane; N-(3-triethoxysilylpropyl)methoxyethoxyethoxy ethyl carbamate; N-(3-triethoxysilylpropyl)methoxyethoxyethoxyethyl carbamate; silane functional (meth)acrylates (e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy)propenyltrimethoxysilane, and 3-(methacryloyloxy)propyltrimethoxysilane)); polydialkylsiloxanes (e.g., polydimethylsiloxane); arylsilanes (e.g., substituted and unsubstituted arylsilanes); alkylsilanes (e.g., substituted and unsubstituted alkyl silanes (e.g., methoxy and hydroxy substituted alkyl silanes)), and the like, or combinations thereof.

In one embodiment, the surface modifying agent for the nanoparticles is an unsubstituted alkyl silane, where the nanoparticles are considered unsubstituted alkyl silane functionalized silica nanoparticles after chemical modification. "Unsubstituted alkyl silane" refers to the chemical modification of a silica nanoparticle with an unsubstituted alkyl silane (e.g., isooctyltrimethoxy silane) as similarly described in U.S. Pat. No. 6,586,483 (Kolb et al.).

For example, silica nanoparticles can be modified with silane functional (meth)acrylates as described, for example, in U.S. Pat. No. 4,491,508 (Olson et al.), U.S. Pat. No. 4,455,205 (Olson et al.), U.S. Pat. No. 4,478,876 (Chung), U.S. Pat. No. 4,486,504 (Chung), and U.S. Pat. No. 5,258,225 (Katsamberis). Surface-modified silica nanoparticles include, for example, silica nanoparticles surface modified with silane surface modifying agents (e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof). Silica nanoparticles can be treated with a number of surface modifying agents (e.g., alcohol, organosilane (e.g., alkyltrichlorosilanes, trialkoxyarylsilanes, trialkoxy(alkyl)silanes, and combinations thereof), and organotitanates, and the like, and mixtures thereof). In one embodiment, a suitable organosilane surface modifying agent can be a trialkoxy silane derivatized poly(ethylene)glycol comprising glycol available commercially from Momentive Performance Materials of Friendly, W. Va.

Nanoparticle surfaces can be modified with organic acid surface-modifying agents which include, for example, oxyacids of carbon (e.g., carboxylic acid), sulfur and phosphorus, acid derivatized poly(ethylene)glycols (PEGs), and the like, and combinations of any of these. Suitable phosphorus containing acids include, for example, phosphonic acids (e.g., octylphosphonic acid, laurylphosphonic acid, decylphosphonic acid, dodecylphosphonic acid, and octadecylphosphonic acid), monopolyethylene glycol phosphonate and phosphates (e.g., lauryl or stearyl phosphate). Suitable sulfur containing acids include, for example, sulfates and sulfonic acids including dodecyl sulfate and lauryl sulfonate. Any such acids may be used in either acid or salt forms.

Non-silane surface modifying agents include, for example, acrylic acid, methacrylic acid, beta-carboxyethyl acrylate, mono-2-(methacryloyloxyethyl)succinate, mono(methacryloyloxypolyethyleneglycol)succinate, and the like, and combinations of one or more of such agents. In another embodiment, surface modifying agents incorporate a carboxylic acid functionality such as $CH_3O(CH_2CH_2O)_2CH_2COOH$, 2-(2-methoxyethoxy)acetic acid having the chemical structure $CH_3OCH_2CH_2OCH_2COOH$, mono(polyethylene glycol) succinate in either acid or salt form, octanoic acid, dodecanoic acid, steric acid, acrylic and oleic acid or their acidic derivatives. In a further embodiment, surface modified iron oxide nanoparticles include those modified with endogenous fatty acids (e.g., stearic acid) or fatty acid derivatives using endogenous compounds (e.g., stearoyl lactylate or sarcosine or taurine derivatives). Further, surface modified zirconia nanoparticles include a combination of oleic acid and acrylic acid adsorbed onto the surface of the particle.

Organic base surface modifying agents for nanoparticles include, for example, alkylamines (e.g., octylamine, decylamine, dodecylamine, octadecylamine, and monopolyethylene glycol amines).

Surface-modifying alcohols and thiols may also be employed including, for example, aliphatic alcohols (e.g., octadecyl, dodecyl, lauryl and furfuryl alcohol), alicyclic alcohols (e.g., cyclohexanol), and aromatic alcohols (e.g., phenol and benzyl alcohol), and combinations thereof. Thiol-based compounds are especially suitable for modifying cores with gold surfaces.

Surface-modified nanoparticles are generally selected in such a way that mixtures comprising dispersed nanoparticles formed are free from a degree of particle agglomeration or aggregation that would interfere with the solute crystallization from the mixture. The surface-modified nanoparticles are generally selected to be either hydrophobic or hydrophilic such that, depending on the character of the solute of the solution for mixing with the nanoparticles of the dispersion, the resulting crystals exhibit controlled crystal shapes and a crystal size distribution.

Suitable surface groups modifying the surface of the plurality of nanoparticles can be selected based upon the nature of the solution comprising the solute, and the crystal shape and/or crystal size distribution desired. The surface modifying groups are selected such that the nanoparticles can be dispersed in the mixture substantially free of aggregation or agglomeration.

A variety of methods are available for modifying the surfaces of nanoparticles. A surface modifying agent can, for example, be added to nanoparticles (e.g., in the form of a powder or a colloidal dispersion) and the surface modifying agent may be allowed to react with the nanoparticles. Multiple synthetic sequences to bring the nanoparticle together with the surface modifying group are plausible. Surface modification processes are described, for example, in U.S. Pat. No. 2,801,185 (Iler), U.S. Pat. No. 4,522,958 (Das et al.) and U.S. Pat. No. 6,586,483 (Kolb et al.).

In the method of the present disclosure, a mixture is formed by combining the solution comprising the solute, and the dispersion comprising nanoparticles. The nanoparticles of the mixture remain substantially dispersed in the mixture, and the solute remains dissolved in the mixture at or below a saturation concentration. The solute remains dissolved in the mixture at the prescribed processing conditions (e.g., heating). The first solvent of the solution and the second solvent of the dispersion are mutually miscible. The first solvent and the second solvent form a single phase.

The mixture comprises dispersed nanoparticles and a dissolved solute. Selection of the first solvent can influence the solubility of the solute and the dispersibility of the nanoparticles in the mixture. The second solvent is provided to disperse the nanoparticles in the dispersion. The second solvent is selected such that when the dispersion is combined with the solution, the solute remains dissolved in the mixture. The nanoparticles are stabilized in the mixture so they do not precipitate or flocculate from the mixture. The mixture can be affected (e.g., by cooling or evaporation) for the solute to exceed the saturation concentration. The crystals form in the presence of the dispersed nanoparticles, and the crystals are separated from the mixture. The nanoparticles remain dispersed in the solvents of the mixture.

After combining the solution and the dispersion to form a mixture, the mixture can be mixed by different techniques. Some examples of mixing techniques include, for example, agitation, stirring, sonicating, and the like, or combinations thereof. As the mixture is mixing, the nanoparticles of the mixture remain dispersed, and the saturation concentration of the solute is exceeded forming crystals in the presence of the dispersed nanoparticles. The crystals are separated from the mixture.

In one embodiment, the concentration of nanoparticles (e.g., unmodified and/or surface modified) in the mixture is in a range of about 0.001 weight percent to about 5 weight percent based on the weight of the nanoparticles to the weight of the solute in the mixture. In some embodiments, the concentration of nanoparticles in the mixture is at least about 0.01 weight percent, at least about 0.1 weight percent, or at least about 0.15 weight percent. In some embodiments, the concentration of nanoparticles in the mixture is no greater than about 4.5 weight percent, no greater than about 4 weight percent, no greater than about 3 weight percent, or no greater than about 2.5 weight percent based on the weight of the nanoparticles to the weight of the solute in the mixture. In other embodiments, the concentration of the nanoparticles in the mixture is in a range of about 0.01 to about 4.5 weight percent, in a range of about 0.1 to about 3 weight percent, or in a range of about 0.15 to about 2.5 weight percent, at least 0.01 weight percent to about 4 weight percent, or at least 0.1 weight percent to about 2 weight percent based on the weight of the nanoparticles to the weight of the solute in the mixture.

In the methods of the present disclosure, cooling is provided to the mixture so that the solute exceeds the saturation concentration. In another aspect, the first solvent or the second solvent is evaporated from the mixture so that the solute exceeds the saturation concentration. When the solute exceeds the saturation concentration, crystals are formed in the presence of the dispersed nanoparticles. The term "solute exceeds the saturation concentration" refers to the supersaturated solution described above.

Saturated and supersaturated solutions can be formed by several techniques. Suitable concentrations of the solute in the mixture in the presence of nanoparticles can be partially dependent on the solubility of the solute in the mixture. At or above a saturation concentration of the solute in the mixture, the solution can be solute crystals. At or above the saturation concentration, the solute can not be in an equilibrium state. A fraction of the solute can remove itself to satisfy the saturation condition of the new mixture. Some techniques for forming supersaturated solutions include cooling, evaporating solvents, drowning out by the addition of a nonsolvent, or reaction crystallization.

In some embodiments, another solvent can be added to the mixture to affect the saturation limit of the solute in the mixture. For example, another solvent (e.g., methanol, ethanol, isopropanol) can be added to the mixture such that the solubility of the solute decreases. As the saturation concentration changes, crystals can be formed in the presence of the dispersed nanoparticles.

Some examples of other solvents which can effect the solubility limit of the solute can include, for example, with water include ethanol, methanol, acetone, isopropanol, toluene, xylene, dichloromethane, dichloroethane, tert-butyl methyl ether, methyl isobutyl ketone, or combinations thereof.

In one aspect, a first solvent and a third solvent (e.g., a blend of solvents) dissolves the solute. The first solvent and the third solvent are mutually miscible. The blend of solvents are mutually miscible with the second solvent dispering the nanoparticles. Solvent can be evaporated from the mixture comprising crystals. Solvent from the blend of solvents (e.g., first solvent and/or the third solvent) can be removed from the mixture or the second solvent can be removed to affect the crystal formed in some embodiments, a portion of the combination of solvent described above for the mixture can be evaporated such that the saturation concentration for forming crystals can be achieved.

Another technique useful for forming supersaturated solutions includes decreasing the temperature of the mixture. The temperature of the mixture can be elevated to increase the solubility of the solute in the first solvent and within the mixture. In some embodiments, the solute is added to the first solvent at an elevated temperature so that the solute remains at or below the saturation concentration. The temperature of the mixture after combining with the dispersion can be decreased so that the solute exceeds the saturation concentration and forms a supersaturated solution. In some embodiments, the temperature of the mixture can be lowered such that crystals form in the presence of the dispersed nanoparticles.

Another technique for forming supersaturated solutions includes removing at least a portion of a first solvent or a second solvent from the mixture. As solvent is removed, the concentration of the solute of the mixture increases forming a supersaturated solution. Some examples of ways to remove solvent include, for example, using evaporation, using reduced pressure, or using elevated temperatures, and the like, or combinations thereof.

Supersaturation of a solute in a solvent is the prerequisite for nucleation and growth of crystals as described in *Crystallization Technology Handbook*, ed. A. Mersmann, Marcel Decker, Inc., New York, 1995 and *Industrial Crystallization from Solutions*, Nyvlt, J., CRC Press, Butterworth & Company, 1971. The qualities of the crystals formed during crystallization (e.g., crystal size distribution, median crystal size, purity and crystal shape) are strongly influenced by the type of crystallization environment (e.g., vessel), the geometry of the vessel, the operating conditions for crystallization to occur, and the properties of the liquid and solid phases.

In the method of the present disclosure, crystals are formed in the presence of nanoparticles. The nanoparticles are dispersed in the mixture during crystal formation. When the solute exceeds the saturation concentration, crystals are formed having a controlled crystal size and a crystal size distribution.

In one embodiment, the crystals are formed by cooling the mixture. As the mixture is cooled, the solute can exceed the saturation concentration in the presence of dispersed nanoparticles. In another embodiment, the crystals are formed by evaporating the first solvent or the second solvent from the mixture. As the first solvent or the second solvent is removed from the mixture, the solute exceeds the saturation concentration in the presence of dispersed nanoparticles.

The crystals formed in the presence of the dispersed nanoparticles of the present disclosure can be separated from the mixture. The nanoparticles of the mixture remain dispersed in the mixture. Experimental analysis by x-ray diffraction suggests that the crystals formed by the method are substantially free of nanoparticles. Nanoparticles are substantially absent from the solute crystals when analyzed by x-ray diffraction (e.g., detection limit to about 1 weight percent).

The crystals generally formed from the mixture have a controlled morphology. The crystals typically have a controlled crystal size distribution and a controlled crystal size rather than a random crystal product. The size and the distribution of crystals can be influenced by the control of the local and mean supersaturation of the mixture as well as the time of the solid in the mixture. As the solute of the mixture exceeds the saturation concentration, the crystallization kinetics influence how the crystals nucleate and grow as well as contribute to the formation of crystals, and the distribution and size of the crystals. The extent of supersaturation of the solute in the mixture can be determined by the flow of the materials and their associated energies. The quality of the solute crystals of solute can depend on the process of micro-mixing on a molecular scale.

The morphologies of the solute crystals formed in the presence of nanoparticles can be controlled relative to solute crystals formed in the absence of nanoparticles. Processes described herein can be used to alter the crystal morphology of solute molecules.

Techniques such as electron microscopy and optical microscopy can be utilized for analyzing the dimensions of crystals formed by the method of the present disclosure. The crystal size of the solute crystals can be in the range of about 0.5 micrometer to about 500 micrometers. In some embodiments, the crystal size can be at least about 1 micrometer, at least about 10 micrometers, at least about 20 micrometers, at least about 30 micrometers, at least about 40 micrometers, at least about 50 micrometers, or at least about 75 micrometers. In some embodiments, the crystal size can be up to about 400 micrometers, up to about 350 micrometers, up to about 300 micrometer, up to about 250 micrometers, up to about 225 micrometers, up to about 200 micrometers, or up to about 150 micrometers. In other embodiments, the crystal size of the solute crystals can be in a range of about 1 micrometer to about 400 micrometers, in a range of about 10 micrometers to about 350 micrometers, in a range of about 20 micrometers to about 300 micrometers, in a range of about 30 micrometers to about 250 micrometers, in a range of about 40 micrometers to about 225 micrometers, in a range of about 50 micrometers to about 200 micrometers, or in a range of about 75 micrometers to about 150 micrometers.

In some embodiments, the crystal shapes of the crystals formed in the presence of nanoparticles can be altered. For example, the aspect ratio of the crystals formed in the presence of the nanoparticles can be changed. The aspect ratio may decrease or increase. In some embodiments, the shape of the crystals range from needlelike to cubic.

In some embodiments, a crystal can be described having three dimensions. In some embodiments, the crystal can have dimensions in three orthogonal directions (e.g., normal to the plane of the crystal, and in each of two orthogonal directions along the plane of the crystal) are equal. In some embodiments, the crystal dimensions can be such that for one dimension in one or more directions is somewhat longer, or even much longer, than the dimensions in the other direction or directions. In some embodiments, the crystal can be such that the one dimension in one or more directions is somewhat shorter, or even much shorter, than the dimensions in the other direction or directions. For example, a crystal can have a needlelike structure. The needlelike crystal can have one dimension somewhat longer than the dimensions in the other direction or directions. For example, a crystal having a cubic structure can have three dimensions somewhat similar to one another. In another example, a crystal can have a platelike structure. The platelike crystal can have two dimensions somewhat similar to one another than the dimension in another direction.

In one embodiment, the crystals are formed in the mixture, and separated from the nanoparticles dispersed in the mixture. The crystals can be separated from the nanoparticles using decantation, filtration, centrifugation, and the like, or combinations thereof. In one embodiment, the crystals of the solute can be washed with a solvent which does not dissolve the solute or change the crystals.

The method of crystallization of the present disclosure can be utilized to form solute crystals having controlled morphologies such as controlled crystal sizes and controlled crystal size distributions. The solute crystals can be combined with active pharmaceutical ingredients for forming pharmaceutical formulations. Suitable active pharmaceutical ingredients include, for example, analgesics, anginal preparations, anti-inflammatories, diuretics, anticholinergics, hormones, xanthines, therapeutic proteins and peptides, and the like, or combinations thereof. Other applications for using the solute crystals formed by the method of the present disclosure include, for example, drug synthesis, protein crystallization, purification, isomeric purification or isolation, polymer synthesis, inorganic/ceramic material synthesis and inorganic/organic hybrid materials, and minerals. Further applications of the solute crystals include, for example, as adjuvants, pigments, colorants, fillers, inorganic salts, and organic salts and the like, or combinations thereof.

The disclosure will be further clarified by the following examples which are exemplary and not intended to limit the scope of the disclosure.

EXAMPLES

The present disclosure is more particularly described in the following examples that are intended as illustrations only, since numerous modifications and variations within the scope of the present disclosure will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

Optical Microscopy

The mixture containing the crystals after mixing was placed onto a glass slide with a disposable pipette. The mixture placed on the slide was covered with a 22 mm×50 mm glass cover slip. The optical micrographs described herein were transmitted oblique polarizer (TOP) images taken using a 5×/0.15 calibration and a 10×/0.30 objective on a Zeiss Axioplan with a Leica DC300 and Twain 32 (Carl Zeiss Microimaging, Incorporated, Thornwood, N.Y.)

X-Ray Diffraction

The crystals of the mixture and the mixtures after separating the crystals were analyzed by x-ray diffraction. These samples were prepared on zero background holders composed of single crystal quartz. Reflection geometry date was collected in the form of a survey scan using a Philip vertical diffractometer, copper $K_\alpha$ radiation, and proportional detector registry of the scattered radiation. The diffractometer was fitted with variable beam slits, fixed diffracted beam slits, and a graphite diffracted beam monochromator. The survey was conducted from 5 to 80 degrees (2Θ) using a 0.04 degree step size and 4, 45, or 60 second dwell times. X-ray generator settings of 45 kV/35 mA were employed.

Preparatory Examples 1A-7

Preparatory Example 1A (PE 1A)

Surface modified nanoparticles were formed from the reaction of a functionalized silane with silica nanoparticles having an average diameter of 21 nanometers (nm). More specifically, 50.1 grams of Nalco 2327 colloidal silica (41.45 weight percent) commercially available from Nalco Chemical Company of Naperville, Ill., and 4.48 grams of the functionalized silane under the trade designation SILQUEST A-1230 commercially available from Momentive Performance Chemicals of Friendly, W. Va., were placed in a round bottom flask equipped with a mechanical stirrer. A water cooled condenser and glass stoppers were attached to the round bottom flask. The flask with stirring was placed in an oil bath heated to 80° C. The contents of the flask were reacted for about 4 hours for forming Preparatory Example 1A. A sample of the surface modified colloidal silica in water was placed in an oven at 130° C. to record the percent solids. The percent solids of the surface modified nanoparticles was about 43.5 weight percent.

Preparatory Example 1B (PE 1B)

Preparatory Example 1B was similarly prepared by the procedure of Preparatory Example 1A, except for forming surface modified nanoparticles using 100 grams of Nalco 2327 available from Nalco Chemical Company, and 6.42 grams of the functionalized silane, SILQUEST A-1230.

Preparatory Example 2A (PE 2A)

Surface modified nanoparticles were formed from the reaction of a functionalized silane with silica nanoparticles having an average diameter of 5 nanometers (nm). More specifically, 600 grams of Nalco 2326 colloidal silica (16.54 weight percent) commercially available from Nalco Chemical Company of Naperville, Ill., and 61.58 grams of the functionalized silane under the trade designation SILQUEST A-1230 commercially available from Momentive Performance Chemicals of Friendly, W. Va., were placed in a round bottom flask equipped with a mechanical stirrer. A water cooled condenser and glass stoppers were attached to the round bottom flask. The flask with stirring was placed in an oil bath heated to 80°

C. The contents of the flask were reacted for about 4 hours for forming Preparatory Example 2A. Infrared spectroscopy was used to follow the completion of the reaction. A sample of the surface modified colloidal silica in water was placed in an oven at 130° C. to dry the material.

Preparatory Example 2B (PE 2B)

Preparatory Example 2B was similarly prepared by the procedure of Preparatory Example 2A, except for forming surface modified nanoparticles using 1000 grams of Nalco 2326 colloidal silica (16.37 weight percent), and 143.24 grams of SILQUEST A-1230.

Preparatory Example 3 (PE 3)

Synthesis of methoxyethoxyethoxyethoxyureidopropyltriethoxysilane (MPEG 3) silane was described in U.S. Pat. No. 6,586,483 (col. 16, line 12).

Surface modified nanoparticles were formed from the reaction of a functionalized silane with silica nanoparticles having an average diameter of 5 nanometers (nm). More specifically, 100.1 grams of Nalco 2326 colloidal silica (16.54 weight percent solids) as described above, 50 grams of ethanol (99%; Sigma-Aldrich, St. Louis, Mo.), and 8.44 grams of the functionalized silane (MPEG 3 silane) were placed in a round bottom flask equipped with a mechanical stirrer. A water cooled condenser and glass stoppers were attached to the round bottom flask. The flask with stirring was placed in an oil bath heated to 80° C. The contents of the flask were reacted for about 20 hours. Ethanol was removed from the solution with a roto-evaporator. A sample of the surface modified colloidal silica was placed in an oven at 150° C. to remove residual ethanol. The percent solids of the surface modified nanoparticles was about 15.83 weight percent.

Preparatory Example 4A (PE 4A)

Surface modified nanoparticles were formed from the reaction of a functionalized silane with silica nanoparticles having an average diameter of 21 nanometers (nm). More specifically, 100.03 grams of Nalco 2327 colloidal silica (41.45 weight percent) as described above, 4.18 grams of isooctyltrimethoxysilane (iC8) commercially available from Gelest Incorporated of Morrisville, Pa., and 65 grams of 1-methoxy-2-propanol (99%; Sigma-Aldrich; St. Louis, Mo.) were placed in a round bottom flask equipped with a mechanical stirrer. An additional 65 grams of 1-methoxy-2-propanol was added to the round bottom flask prior to heating the flask. A water cooled condenser and glass stoppers were attached to the round bottom flask. The flask with stirring was placed in an oil bath heated to 80° C. The contents of the flask were reacted for about 20 hours forming Preparative Example 4A. The surface modified colloidal silica was placed in an oven at 150° C. till dry. The dried product was re-dispersed as a 10 weight percent solution in toluene to determine dispersibility. The surface modified nanoparticles were dispersed uniformly resulting in a clear solution. A sample of the surface modified colloidal silica in water was placed in an oven at 130° C. to record the percent solids. The percent solids of the surface modified nanoparticles was about 43.5 weight percent.

Preparatory Example 4B (PE 4B)

Preparatory Example 4B was similarly prepared by the procedure of Preparatory Example 4A, except for forming surface modified nanoparticles using 100.03 grams of Nalco 2327 colloidal silica (41.45 weight percent) and 5.82 grams of iC8 as described above.

Preparatory Example 5A (PE 5A)

Surface modified nanoparticles were formed from the reaction of a functionalized silane with silica nanoparticles having an average diameter of 5 nanometers (nm). More specifically, 500.0 grams of Nalco 2326 colloidal silica (16.14 weight percent) as described above, 450 grams of ethanol, and 112.5 grams of methanol (both available from Sigma-Aldrich, St. Louis, Mo.), and 33.1 grams of isooctyltrimethoxysilane (iC8) commercially available from Gelest Incorporated of Morrisville, Pa., were placed in a round bottom flask equipped with a mechanical stirrer. A water cooled condenser and glass stoppers were attached to the round bottom flask. The flask with stirring was placed in an oil bath heated to 80° C. The contents of the flask were reacted for about 20 hours. The surface modified colloidal silica was placed in an oven at 150° C. until dry. The dried product was re-dispersed as a 10 weight percent solution in toluene to determine dispersibility. The surface modifice nanoparticles were dispersed uniformly resulting in a clear solution. A sample of the surface modified colloidal silica in water was placed in an oven at 130° C. to remove residual ethanol.

Preparatory Example 5B (PE 5B)

Preparatory Example 5B was similarly prepared by the procedure of Preparatory Example 5A, except for forming surface modified nanoparticles using 50.0 grams of Nalco 2326 colloidal silica (16.07 weight percent), 45 grams of 1-methoxy-2-propanol, and 4.44 grams of iC8.

Preparatory Example 6 (PE 6)

Surface modified nanoparticles were formed from the reaction of a functionalized silane with silica nanoparticles having an average diameter of 5 nanometers (nm). More specifically, 100.1 grams of Nalco 2326 colloidal silica (16.14 weight percent) as described above, and 11.13 grams of octyldecyltrimethoxysilane (C18) commercially available from Gelest Incorporated of Morrisville, Pa., and 65 grams of 1-methoxy-2-propanol (99%; Sigma-Aldrich; St. Louis, Mo.) were placed in a round bottom flask equipped with a mechanical stirrer. After the above materials were stirred, an additional 65 grams of 1-methoxy-2-propanol was added to the flask. A water cooled condenser and glass stoppers were attached to the round bottom flask. The flask with stirring was placed in an oil bath heated to 80° C. The contents of the flask were reacted for about 20 hours. A sample of the surface modified colloidal silica in water was placed in an oven at 130° C. to dry the product. The dried product was redispersed as a 1 percent solution in toluene. The product dispersed well in toluene producing a clear solution.

Preparatory Example 7 (PE 7)

Surface modified nanoparticles were formed from the reaction of a functionalized silane with silica nanoparticles having an average diameter of 21 nanometers (nm). More specifically, 100.1 grams of Nalco 2327 colloidal silica (41.45 weight percent) as described above, and 7.03 grams of octyldecyltrimethoxysilane (C18) commercially available from Gelest Incorporated of Morrisville, Pa., and 120 grams of 1-methoxy-2-propanol (99%; Sigma-Aldrich; St. Louis, Mo.) were placed in a round bottom flask equipped with a mechanical stirrer. A water cooled condenser and glass stoppers were attached to the round bottom flask. The flask with stirring was placed in an oil bath heated to 80° C. The contents of the flask were reacted for about 20 hours. A sample of the surface modified colloidal silica in water was placed in an oven at 130° C. to dry the product. The dried product was redispersed as a 1 percent solution in toluene. The product dispersed well in toluene producing a clear solution.

Comparative Examples 1 (CE 1) and Examples 1-12

Samples comprising a solute and nanoparticles were prepared. About 62.5 grams of lactose (D-(+)-lactose (Mallinckrodt Baker, Incorporated; Phillipsburg, N.J.)) was added to about 100 grams of deionized water and heated to about 70° C. in a flask to form a clear solution. The solution was then heated to about 80° C. An additional 2.5 grams of lactose was dissolved in deionized water to provide a clear solution. The solution was then combined with a nanoparticle dispersion (listed in Table 1) to form a mixture in a glass container. In the mixture, the solute remained dissolved, and the nanoparticles remained dispersed in the mixture. The glass container was sealed and placed on a roller for about 20 hours.

Lactose crystals were formed in the mixture. The lactose crystals were separated from the mixture by settling, and then decanting the mixture from the crystals. The crystals were analyzed by optical microscopy. The optical micrographs of the lactose crystals (FIGS. 1-3) have a 200 micrometer marker for approximating crystal sizes. Samples were analyzed by X-ray diffraction for the presence of nanoparticles. X-ray diffraction analyses indicated the absence of nanoparticles in the lactose crystals formed in Examples 1-12.

Table 1 illustrates crystals formed in Comparative Example 1 and Examples 1-12 in the absence of nanoparticles, or in the presence of unmodified nanoparticles, or in the presence of surface modified nanoparticles. Each example details the preparatory nanoparticle dispersion used with the solute to be crystallized. The content of nanoparticles present in the mixture ranged from 0.10 to 1 weight percent based on the weight of the nanoparticles to the weight of the lactose in the mixture. Crystal size range evaluations were based on individual crystals present in a given micrograph. Crystal size distributions were based on the size of single crystals present in a given micrograph. Table 1 further includes the formation of satellite crystals, twinned crystals, and combinations thereof.

FIG. 1 is an optical micrograph of Comparative Example 1 illustrating lactose crystals formed without nanoparticles.

Figure 2:
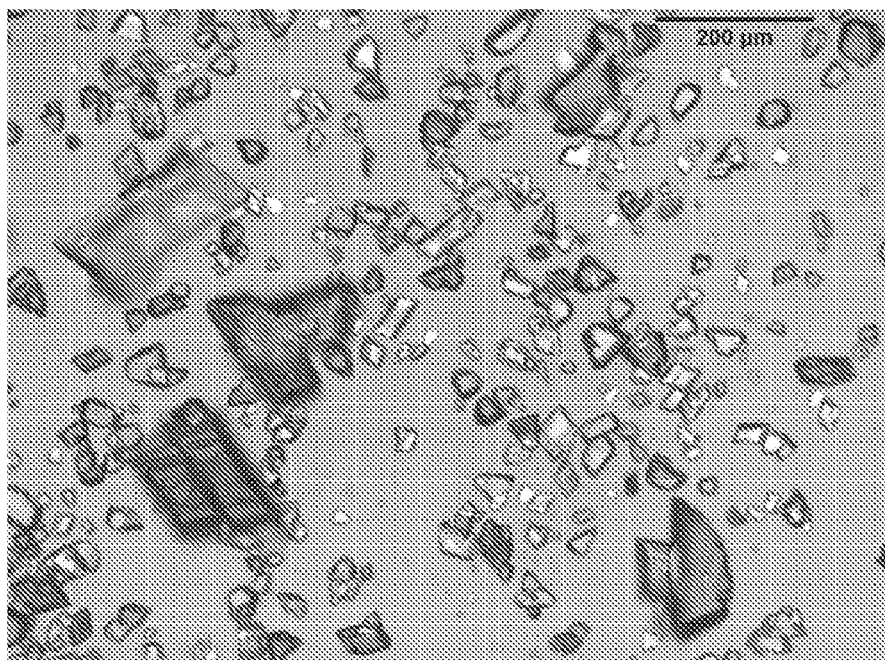
FIG. 2 is an optical micrograph of lactose crystals formed in the presence of nanoparticles.

FIG. 2 is an optical micrograph of Example 2 illustrating lactose crystals formed in the presence of unmodified nanoparticles. A narrow crystal size distribution and crystal sizes were observed for FIG. 2.

Figure 3:
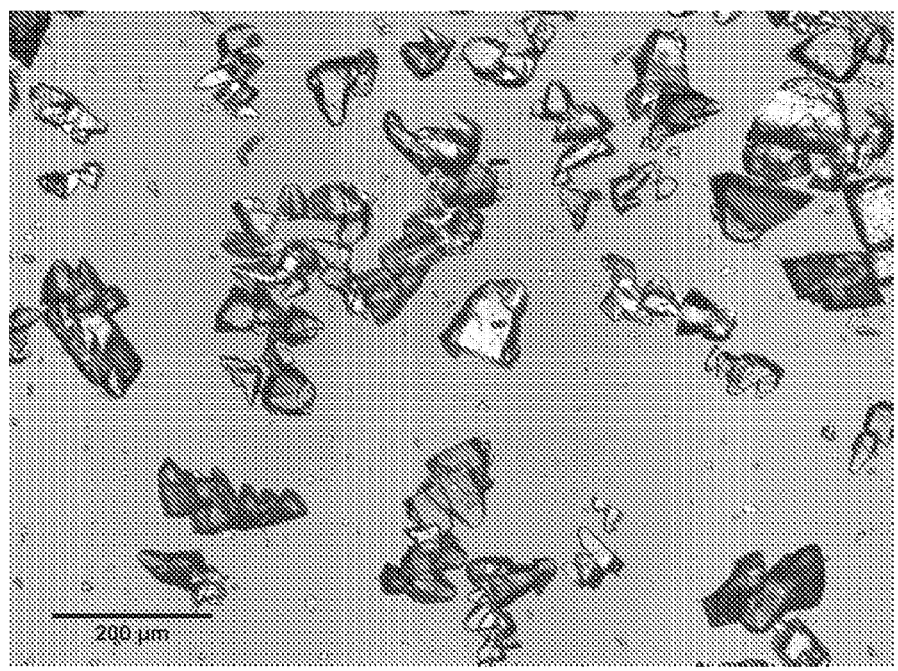
FIG. 3 is an optical micrograph of lactose crystals formed in the presence of surface modified nanoparticles.

FIG. 3 is an optical micrograph of Example 3 illustrating lactose crystals formed in the presence of surface modified nanoparticles. A narrow crystal size distribution was observed. The crystals of Example 3 have a narrow crystal size distribution in comparison to the lactose crystals of Comparative Example 1 (FIG. 1).

Examples 3-12 of Table 1 illustrate the effect of lactose crystal formation in the presence of surface modified nanoparticles at different concentrations, and different nanoparticle surface modifications in the mixtures.

Comparative Example 2 (CE 2) and Example 13-24

Samples comprising a solute and nanoparticles were prepared. About 15.5 grams of triphenylmethanol (Mallinckrodt Baker, Incorporated; Phillipsburg, N.J.)) was added to about 80.63 grams of toluene and heated to about 70° C. in a flask to form a clear solution. The solution was then heated to about 80° C. An additional 0.52 grams of triphenylmethanol was dissolved in toluene to provide a clear solution. The solution was then combined with a nanoparticle dispersion (as listed in Table 2), to form a mixture in a glass container. In the mixture, the solute remained dissolved, and the nanoparticles remained dispersed in the mixture. The glass container was sealed and placed on a roller for about 20 hours.

Triphenylmethanol crystals were formed in the mixture. The triphenylmethanol crystals were separated from the mixture by settling, and decanting the mixture from the crystals. The crystals were analyzed by optical microscopy. The optical micrographs of (FIGS. 4-5) have a 200 micrometer marker for approximating crystal sizes. Samples were analyzed by X-ray diffraction for the presence of nanoparticles. X-ray diffraction analyses indicated the absence of nanoparticles in the triphenylmethanol crystals formed in Examples 15-26.

Table 2 illustrates crystals formed in Comparative Example 2 and Examples 13-24 in the absence of nanoparticles, or in the presence of surface modified nanoparticles. Each sample details the preparatory nanoparticle dispersion used with the solute to be crystallized. The content of nanoparticles present in the mixture ranged from 0.10 to 1 weight percent based on the weight of the nanoparticles to the weight

TABLE 1

| Example | Nanoparticle | Percent Nanoparticles (%) | Crystal size range (μm) | Crystal size distribution (narrow/broad) | Twinning/Satellite crystals |
|---|---|---|---|---|---|
| CE 1 | no nanoparticles | — | 100-500 | broad | Twinning/satellite |
| 1 | 2326 only | 1.00 | 100-400 | broad | |
| 2 | 2326 only | 0.10 | 25-100 | narrow | satelllite |
| 3 | PE 2A | 1.00 | 100-150 | narrow | satellite |
| 4 | PE 2B | 1.00 | 100-250 | narrow | satellite |
| 5 | PE 2A | 0.10 | 200-350 | narrow | satellite |
| 6 | PE 2B | 0.10 | 300-400 | narrow | satellite |
| 7 | PE 3 | 1.00 | 200-450 | broad | satellite |
| 8 | PE 3 | 0.10 | 200-400 | broad | Satellite/twinning |
| 9 | PE 1B | 1.00 | 100-400 | broad | Satellite/twinning |
| 10 | PE 1A | 1.00 | 150-250 | narrow | Satellite |
| 11 | PE 1B | 0.10 | 300-600 | broad | Satellite/twinning |
| 12 | PE 1A | 0.10 | 100-400 | broad | twinning | of triphenylmethanol in the mixture. Crystal size range evaluations were based on individual crystals present in the micrograph. Crystal size distributions were based on the size of single crystals present in a given micrograph. Table 2 further includes the formation of satellite crystals, twinned crystals, and combinations thereof.

TABLE 2

| Example | Nanoparticle | Nanoparticles in mixture (%) | Crystal size range (μm) | Crystal size distribution (narrow/broad) | Twinning/ Satellite crystals |
| --- | --- | --- | --- | --- | --- |
| CE 2 | no nanoparticles | — | 200-500 | broad | Satellite/twinning |
| 13 | PE 5A | 1.00 | 200-500 | broad | Satellite |
| 14 | PE 5A | 0.10 | 200-300 | narrow | twinning |
| 15 | PE 5B | 1.00 | 200-400 | broad | satellite |
| 16 | PE 5B | 0.10 | 150-300 | broad | Twinning/satellite |
| 17 | PE 6 | 1.00 | 100-400 | broad | satellite |
| 18 | PE 6 | 0.10 | 200-250 | narrow | Satellite |
| 19 | PE 4A | 1.0 | 200-300 | narrow | |
| 20 | PE 4A | 0.10 | 100-300 | broad | Twinning |
| 21 | PE 4B | 1.0 | 200-500 | broad | Satellite/twinning |
| 22 | PE 4B | 0.10 | 150-200 | narrow | Twinning |
| 23 | PE 7 | 1.0 | 150-200 | narrow | Twinning |
| 24 | PE 7 | 0.1 | 200-300 | narrow | |

Figure 4:
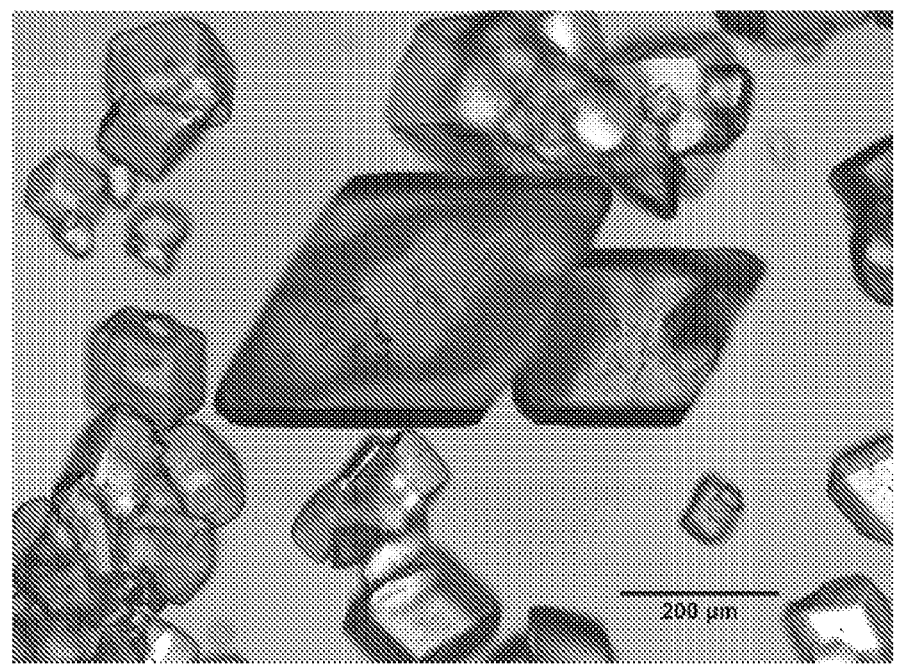
FIG. 4 is an optical micrograph of triphenylmethanol crystals formed in the absence of nanoparticles.

FIG. 4 is an optical micrograph of Comparative Example 2 illustrating triphenylmethanol crystals formed without nanoparticles.

Figure 5:
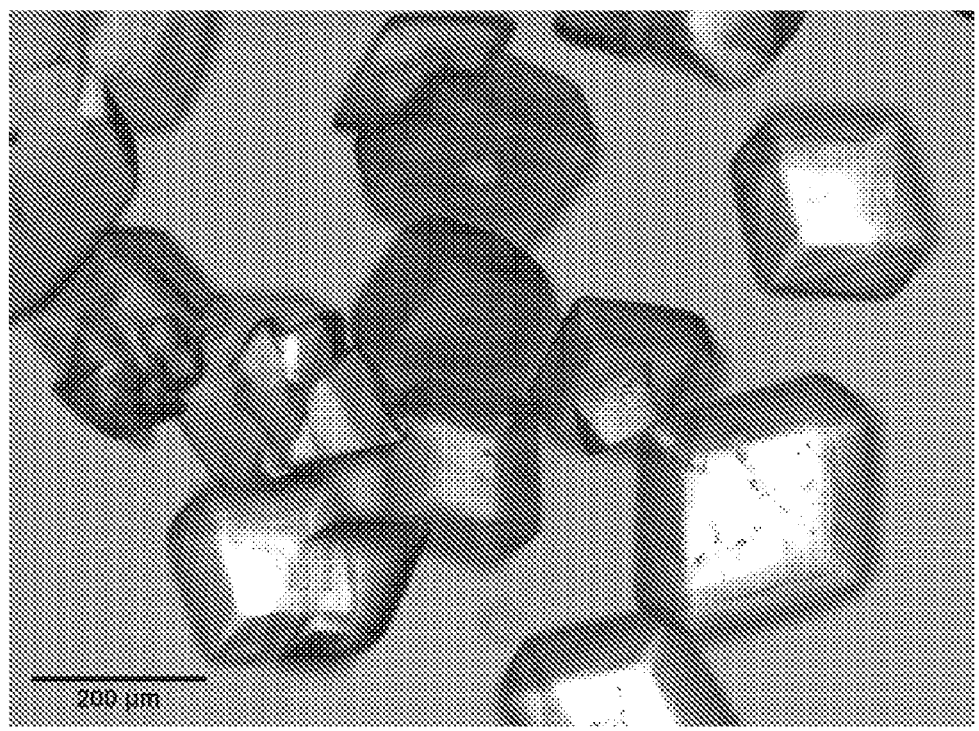
FIG. 5 is an optical micrograph of triphenylmethanol crystals formed in the presence of surface modified nanoparticles.

FIG. 5 is an optical micrograph of Example 14 illustrating triphenylmethanol crystals formed in the presence of surface modified nanoparticles. A narrow crystal size distribution and crystal sizes were observed in FIG. 5 in comparison to the triphenylmethanol crystals formed in Comparative Example 2 (FIG. 4).

Examples 13-24 of Table 2 illustrate the effects of triphenylmethanol crystal formation in the presence of surface modified nanoparticles at different concentrations and different nanoparticle surface modifications in the mixtures.

Various modifications and alterations of this disclosure will be apparent to those skilled in the art without departing from the scope and spirit of this disclosure, and it should be understood that this disclosure is not limited to the illustrative elements set forth herein.

What is claimed is:

1. A method of crystallization comprising:
   providing a solution comprising a solute dissolved in a first solvent;
   providing a dispersion comprising a plurality of nanoparticles in a second solvent, wherein the nanoparticles comprise a surface modified with aliphatic silane groups or polyalkyleneoxidealkoxy silane groups, wherein the first solvent and the second solvent are mutually miscible;
   combining the solution and the dispersion to form a mixture, wherein the nanoparticles remain dispersed in the mixture and the solute remains dissolved in the mixture at or below a saturation concentration;
   cooling the mixture such that the solute exceeds the saturation concentration forming crystals; and
   separating the crystals from the mixture, wherein the nanoparticles remain dispersed in the mixture.

2. The method of claim 1, wherein the solute comprise sugars, alcohols, aromatic esters, active pharmaceutical ingredients, adjuvants, pigments, colorants, fillers, inorganic salts, organic salts, or combinations thereof.

3. The method of claim 2, wherein the solute comprises sugars.

4. The method of claim 3, wherein the solute comprises lactose, lactose monohydrate, maltose, sucrose, or combinations thereof.

5. The method of claim 2, wherein the solute comprises alcohols.

6. The method of claim 5, wherein the solute comprises triphenylmethanol.

7. The method of claim 1, wherein the first solvent is the same as the second solvent.

8. The method of claim 1, wherein the first solvent is different than the second solvent.

9. The method claim 1, wherein the first solvent or the second solvent independently comprise water, an alcohol, an aliphatic hydrocarbon, an aromatic hydrocarbon, a ketone, an ester, a fluorocarbon, a hydrofluorocarbon, a supercritical fluid, or combinations thereof.

10. The method of claim 1, wherein the concentration of the nanoparticles in the mixture is in a range of about 0.01 weight percent to about 5 weight percent.

11. The method of claim 1, further comprising agitating the mixture while cooling the mixture.

12. The method of claim 1, wherein separating comprises decantation, filtration, centrifugation, or combinations thereof.

13. The method of claim 1, further comprising washing the crystals of the solute.

14. The method of claim 1, wherein after separating the crystals from the mixture, the crystals are substantially free of the nanoparticles.

15. The method of claim 1, wherein the crystals have dimensions in a range of about 0.5 micrometers to about 500 micrometers.

16. A method of crystallization comprising:
   providing a solution comprising a solute dissolved in a first solvent;
   providing a dispersion comprising a plurality of nanoparticles in a second solvent, wherein the nanoparticles comprise a surface modified with aliphatic silane groups or polyalkyleneoxidealkoxy silane groups, wherein the first solvent and the second solvent are mutually miscible;
   combining the solution and the dispersion to form a mixture, wherein the nanoparticles remain dispersed in the mixture and the solute remains dissolved in the mixture at or below a saturation concentration;
   evaporating solvent from the mixture such that the solute exceeds the saturation concentration forming crystals; and separating the crystals from the mixture, wherein the nanoparticles remain dispersed in the mixture.

17. The method of claim 16, wherein evaporating comprises evaporating the first solvent and the second solvent.

18. A method of crystallization comprising:
providing a solution comprising a solute dissolved in a first solvent and a third solvent, the first solvent and the third solvent mutually miscible;
providing a dispersion comprising a plurality of nanoparticles in a second solvent, wherein the nanoparticles comprise a surface modified with aliphatic silane groups or polyalkyleneoxidealkoxy silane groups, wherein the first solvent, the third solvent and the second solvent are mutually miscible;
combining the solution and the dispersion to form a mixture, wherein the nanoparticles remain dispersed in the mixture and the solute remains dissolved in the mixture at or below a saturation concentration;
evaporating solvent from the mixture such that the solute exceeds the saturation concentration forming crystals; and
separating the crystals from the mixture, wherein the nanoparticles remain dispersed in the mixture.

19. The method of claim 18, wherein evaporating comprises evaporating the first solvent, the second solvent, and the third solvent.

\* \* \* \* \*

UNITED STATES PATENT AND TRADEMARK OFFICE
CERTIFICATE OF CORRECTION

PATENT NO. : 8,323,360 B2
APPLICATION NO. : 12/993746
DATED : December 4, 2012
INVENTOR(S) : Jimmie R Baran Page 1 of 1

It is certified that error appears in the above-identified patent and that said Letters Patent is hereby corrected as shown below:

Column 9
Line 27, delete "steric" and insert -- stearic --, therefor.

Column 11
Line 29, delete "dispering" and insert -- dispersing --, therefor.

Column 15
Line 49, delete "methyoxy" and insert -- methoxy --, therefor.

Columns 17-18
Line 6, in (Table 1), delete "satelllite" and insert -- satellite --, therefor.

Column 20
Line 31, in Claim 9, delete "method claim" and insert -- method of claim --, therefor.

Signed and Sealed this
Twelfth Day of February, 2013

Teresa Stanek Rea
*Acting Director of the United States Patent and Trademark Office*